(12) United States Patent
Holland

(10) Patent No.: US 7,028,357 B2
(45) Date of Patent: Apr. 18, 2006

(54) PATIENT IMMOBILIZATION AND TRANSPORTATION SYSTEM

(75) Inventor: Michael H. Holland, Norwich, VT (US)

(73) Assignee: Innex Technologies, Inc., Norwich, VT (US)

(*) Notice: Subject to any disclaimer, the term of this patent is extended or adjusted under 35 U.S.C. 154(b) by 28 days.

(21) Appl. No.: 10/808,917

(22) Filed: Mar. 25, 2004

(65) Prior Publication Data

US 2004/0187214 A1    Sep. 30, 2004

Related U.S. Application Data

(60) Provisional application No. 60/457,362, filed on Mar. 26, 2003.

(51) Int. Cl.
*A61G 1/00* (2006.01)

(52) U.S. Cl. .................... 5/626; 5/625; 5/628; 128/870

(58) Field of Classification Search ............ 5/625–629; 128/869, 870
See application file for complete search history.

(56) References Cited

U.S. PATENT DOCUMENTS

| | | | |
|---|---|---|---|
| 3,967,128 A | 6/1976 | Smulewicz ................. 250/444 |
| 4,262,872 A | 4/1981 | Kodet ...................... 248/311.3 |
| 4,895,173 A | 1/1990 | Brault et al. ................ 128/870 |
| 5,032,623 A | 7/1991 | Keske et al. ................ 521/131 |
| 5,088,137 A | 2/1992 | Rose ............................. 5/625 |
| 5,194,175 A | 3/1993 | Keske et al. ............ 252/182.25 |
| 5,274,007 A | 12/1993 | Keske et al. ................ 521/130 |
| 5,366,191 A | 11/1994 | Bekanich ..................... 248/125 |
| 5,414,883 A | 5/1995 | Fangrow, Jr. .................. 5/625 |
| 5,473,784 A * | 12/1995 | Nixon et al. .................... 5/625 |
| 5,560,059 A * | 10/1996 | McQueen ...................... 5/625 |
| 5,568,662 A | 10/1996 | Gougelet ....................... 5/625 |
| 5,771,513 A * | 6/1998 | Kirchgeorg et al. ........... 5/625 |
| 5,950,627 A | 9/1999 | Bologovsky et al. ....... 128/869 |
| 6,138,306 A | 10/2000 | Muhanna ....................... 5/706 |
| 6,443,157 B1 | 9/2002 | Sargent ...................... 128/870 |
| 6,715,170 B1 * | 4/2004 | Richmond ..................... 5/625 |
| 6,915,805 B1 * | 7/2005 | Crutchfield ................ 128/870 |
| 6,954,952 B1 * | 10/2005 | Kroupa ......................... 5/625 |

(Continued)

OTHER PUBLICATIONS

Information on "RediPad" brand foam padding for adhering to backboards, obtained from URL: http://www.ambuusa.com/redipad.htm.

*Primary Examiner*—Robert G. Santos
(74) *Attorney, Agent, or Firm*—Michael J. Weins; Jeffrey E. Semprebon

(57) ABSTRACT

A board has an upper section, with an upper surface for supporting a patient, and a lower section, having two spars separated by a concave surface. The lower section is smaller than the upper section, forming longitudinal flanges through which hand passages are provided. Stiffening members can be housed in the spars. The board is combined with a pad that is attached to the upper surface. A beveled edge on the pad reduces shear forces. Indicia, such as a raised ridge, aid in properly locating the pad, which is preferably attached by a two-sided adhesive sheet with less adhesion on the side that adheres to the board. An IV support pole formed of collapsible segments can be attached to the board by a clamp. The pole has a hook on which an IV container can be hung, and an elastic wrap that encircles, stabilizes, and pressurizes the IV container.

18 Claims, 10 Drawing Sheets

U.S. PATENT DOCUMENTS

| | | | |
|---|---|---|---|
| 2002/0104934 A1 | 8/2002 | Elliott et al. | 248/126 |
| 2003/0200972 A1* | 10/2003 | Crutchfield | 5/625 |
| 2003/0213066 A1 | 11/2003 | Richmond | 5/625 |
| 2004/0187214 A1* | 9/2004 | Holland | 5/626 |

* cited by examiner

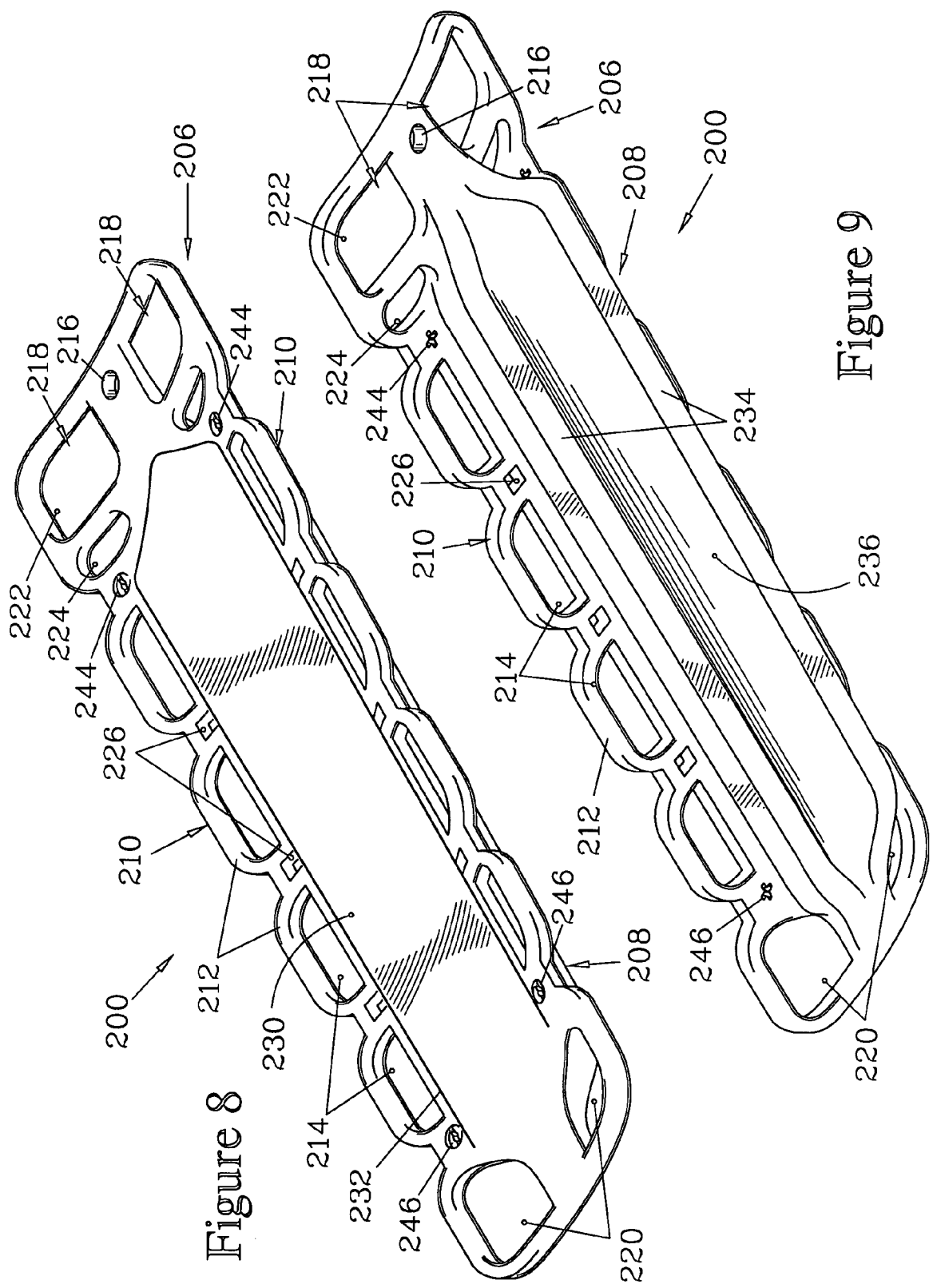

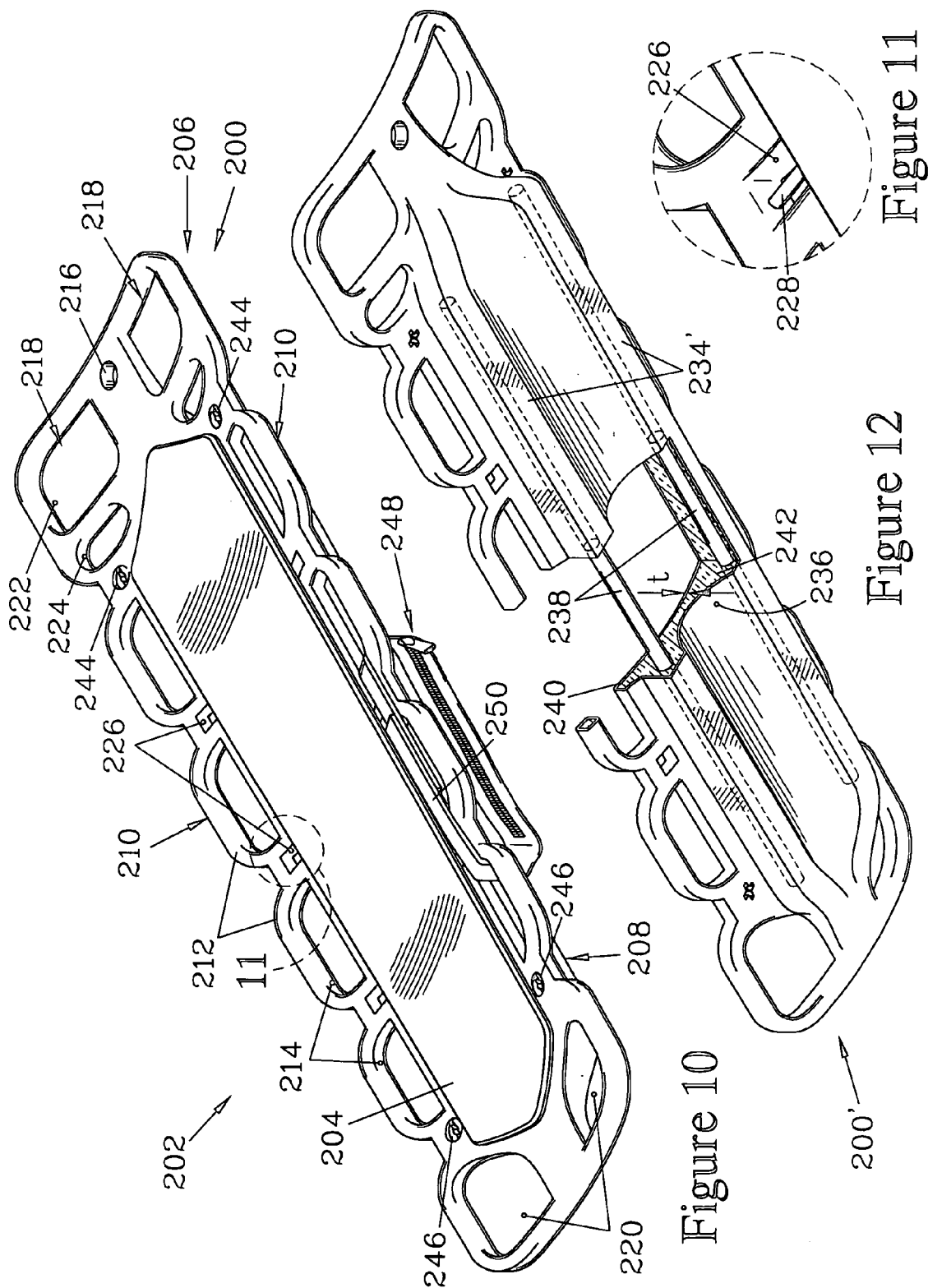

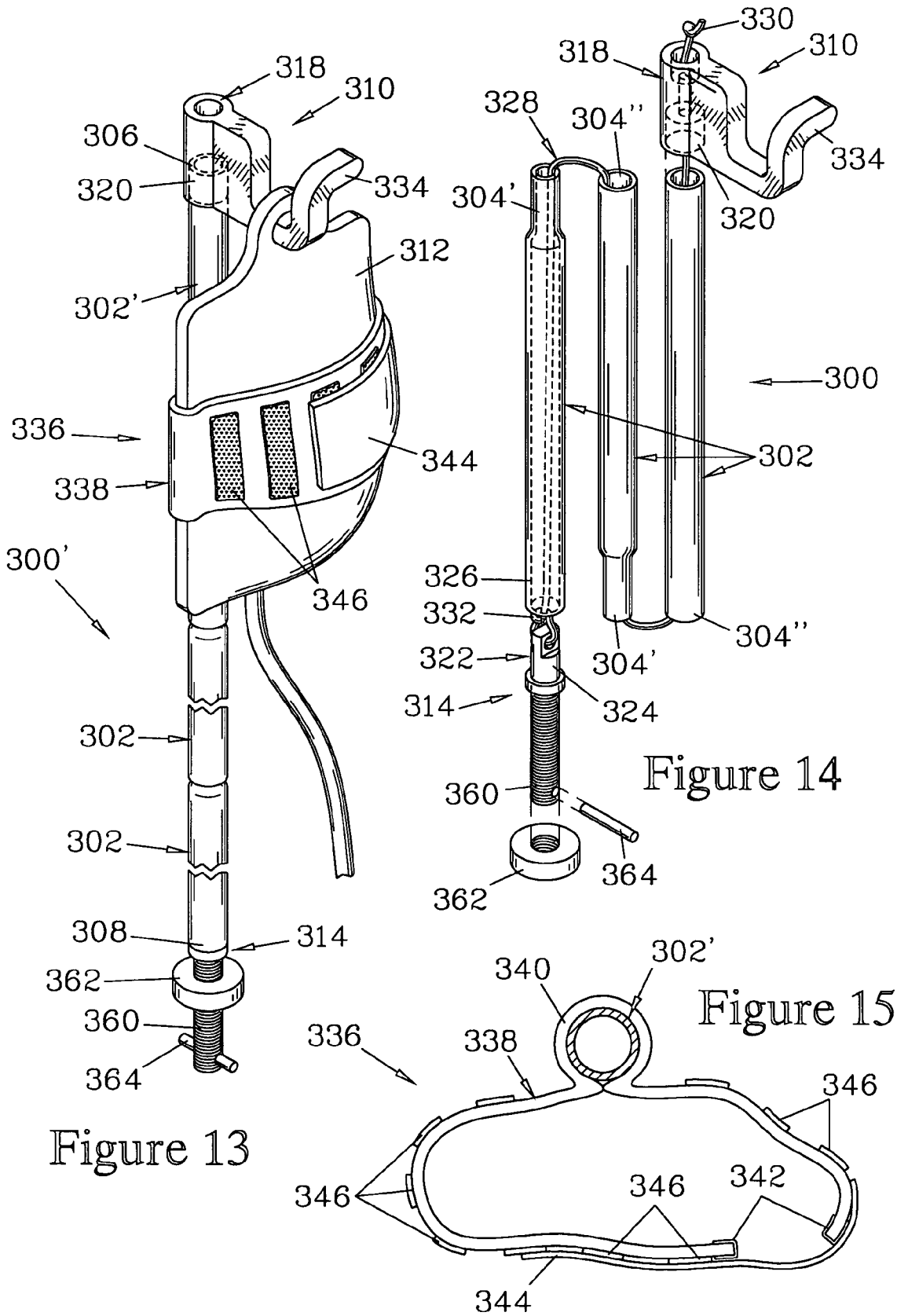

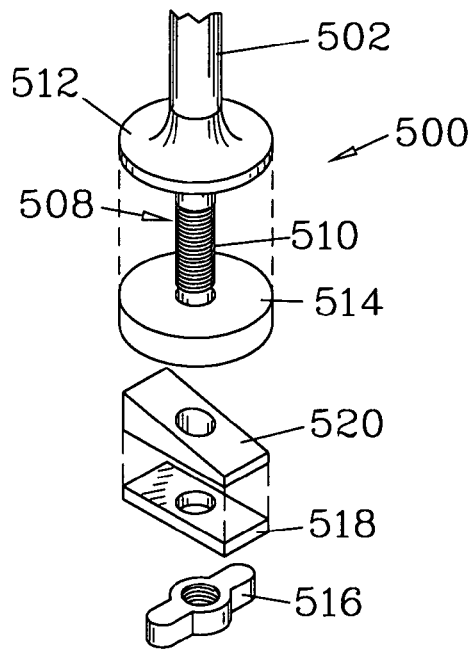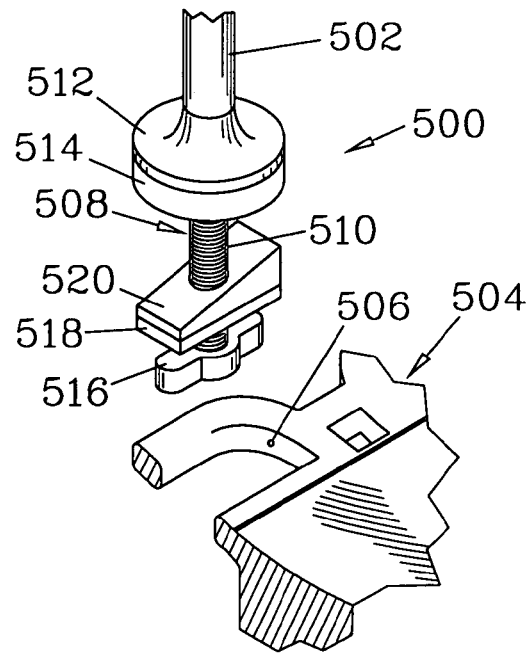
Figure 24
Figure 25
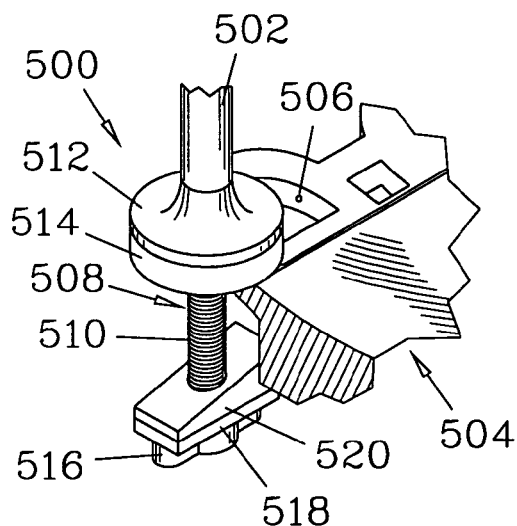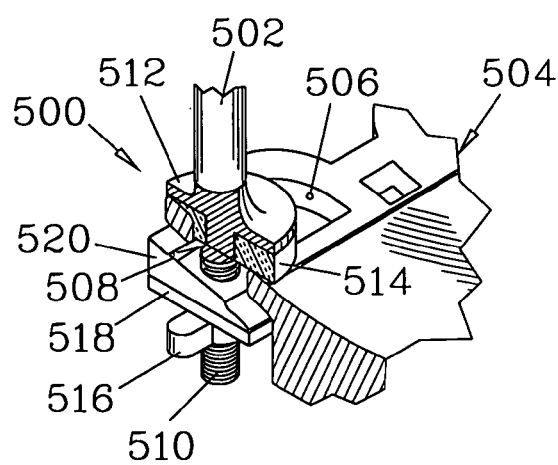
Figure 26
Figure 27

PATIENT IMMOBILIZATION AND TRANSPORTATION SYSTEM

This application claims benefit of U.S. Provisional Application Ser. No. 60/457,362, filed Mar. 26, 2003, titled Spinal Immobilization Device and Method, the disclosure of which is expressly incorporated by reference herein.

FIELD OF THE INVENTION

The present invention relates to boards which are employed to immobilize and transport patients from a remote location to a location where medical treatment can be administered, frequently referred to as spinal boards or back boards.

BACKGROUND OF THE INVENTION

There is often a need to transport a patient from a remote location to a hospital or similar medical care facility. When the patient has suffered injuries such as fractures, it is important to keep the patient relatively immobile to prevent patient movement that might exacerbate the injuries. Classically, the patient is placed upon a board and secured thereto via restraint straps to immobilize the patient. Additional restraining elements, such as devices to cradle the head of the patient, may also be attached to the board. The board provides a rigid support for the patient, and has handgrips to allow transporting personnel to readily grasp and carry the board.

Traditional boards create two problems for care of patients. First, the structure of the board may act to obscure x-rays taken with the patient on the board, even when the board is fabricated from a relatively x-ray transparent material such as plastic. This either requires the patient to be removed from the board, which risks additional injury due to such movement, or results in difficulty interpreting the x-rays, which may compromise the effectiveness of medical treatment. Obscuration of x-rays is particularly a problem when stiffening members are incorporated in the board to provide rigidity and these stiffening members extend across areas where x-rays are likely to be needed. A second problem results when the patient is placed on the board for long periods of time, which can cause severe discomfort due to the patient being secured against a hard surface.

An attempt to overcome both the problems of patient discomfort and obscuration of x-rays is the spinal and cervical immobilization device taught in U.S. Pat. No. 5,568,662. This device employs a board with two beveled indentations, one located in the torso region of the patient and one in the head region. Padding is placed into these indentations to decrease the discomfort of the patient, while the beveled edges are intended to prevent obscuration of x-rays by the indentations. The board is fabricated by a resin transfer molding technique that is apparently intended to provide a board having adequate rigidity without incorporating additional stiffening members. While the padding of the '662 device may reduce discomfort, its placement in indentations makes the board unsuitable for use without the padding, since the beveled edges of the indentations would then create a hard, uneven surface for supporting the patient. In fact, these indentations may cause increased discomfort even when padding is employed, if the padding material is too compressible. The indentations also complicate cleaning and decontamination of the board if it becomes soiled by blood or other bodily fluids.

Another concern for transportation of patients is the provision of intravenous (IV) fluids during transport. U.S. Pat. No. 6,443,157 teaches a board that incorporates a pair of folding support members upon which IV fluid containers may be hung. However, the supports do not appear to be rigidly secured and reside on the periphery of the board, making them susceptible to impact during transport of the patient. Because the supports are not secured, impacts may dislodge the supports, which may then collapse if the board is jarred while being moved over rough terrain or loaded into a vehicle.

There is a need for a patent transportation and immobilization system which can provide immobilization and support of a patient without undue patient discomfort or obscuration of x-rays and which can provide secure support for an IV fluid container.

SUMMARY OF THE INVENTION

The present invention provides a system for the transportation and/or immobilization of an individual or patient. The system has a board for support of the individual. The board has an upper section with an upper section footprint which is substantially symmetrically disposed about a longitudinal axis. The upper section has an upper surface on which the individual is supported. The upper surface is substantially planar, and it is preferred for the upper surface to be slightly concave when viewed from above the board to provide greater comfort to the patient and to better stabilize the patient when supported on the board.

The board also has a lower section, which has a lower section footprint that is smaller than the upper section footprint and is substantially symmetrically disposed about the longitudinal axis, so as to provide longitudinal flanges on the upper section which extend beyond the lower section. Hand passages through the longitudinal flanges provide handgrips for gripping the board. Preferably, strap passages are also provided through the longitudinal flanges to facilitate securing restraint straps to the board.

The lower section terminates in a lower surface central region which is concave when the board is viewed from below. The lower section is further bounded by a pair of spaced apart spars that smoothly join the lower surface central region and the longitudinal flanges. It is preferred for the spaced-apart spars to be defined by substantially L-shaped surfaces and be proportioned such that stiffening members with diameters of up to about 1 inch in diameter can be housed within the spars. Typically, these stiffening members are fabricated from a variety of materials such as fiberglass tubes, carbon filament reinforced tubes, or hickory rods. One example of such stiffening members is carbon graphite tubes, such as taught in U.S. Pat. No. 5,950,627. When the board is formed by rotationally molding a shell with spars sized at least about 1½ inches high and 1 inch wide at the bottom, the spars will house stiffening members of the sizes discussed above. Furthermore, when the shell of such a board has a nominal wall thickness in the neighborhood of about 0.1 inches and is foam filled, this should result in a board which has sufficient rigidity that reinforcing members are not needed except for the most severe loading conditions.

In a preferred embodiment of the present invention, a fluid-impermeable pad is attached to the upper surface of the board to provide a more comfortable surface for supporting the patient. The pad preferably has a periphery configured such that, when the pad is affixed to the upper surface, it substantially covers the region of the upper surface located inward of the hand passages and strap passages, if such are included, so as to provide the maximum area of coverage without obstructing the hand passages and strap passages. It is further preferred that the periphery of the pad be provided with a beveled edge that creates a ramped surface between the board and a front side of the pad. To assure proper alignment, it is further preferred that indicia be provided on the upper surface of the board to form a pad indexing mark to aid a user in symmetrically locating the pad as it is applied to the board and to assure that it remains symmetrically disposed with respect to the hand passages as it is applied. The pad indexing mark can be printed on the upper surface or molded into the upper surface of the board. Alternatively, molded indicia can be formed by grooves or ridges. However, if such is done, it is preferred that the grooves not form a closed circuit or that the ridge not be configured to bound a closed area; care to avoid these conditions when employing grooves and/or ridges promotes flushing of the surface and avoids sites for collection of residual liquid after flushing. When a ridge is used to form the pad indexing mark, it is further preferred that the ridge have a low profile of less than about 0.01 inch so as not to cause discomfort if the board is used when the pad is removed. Having a low profile ridge also assures that the pad, if misaligned with respect to the upper surface of the board, can still firmly attach to the upper surface.

The system of the present invention is preferably fitted with an IV support pole, which also has utility when used in combination with boards other than those described above. In all cases it is preferred to employ an IV support pole that can be maintained in position on the board without unduly restricting the motion of the board. For these reasons, it is preferred that the IV support pole be relatively short and that it mount within the periphery of the board.

The IV support pole is formed from a series of pole segments configured such that, when joined together, they form a rigid extended pole terminating in a pole first free end and a pole second free end. Each of the pole segments has adjoining portions with engaging ends which can readily engage. Preferably, the engaging ends are configured as male ends and female ends where the male ends can slidably engage the female ends and, when so engaged, the pole segments form the rigid extended pole terminating in the pole first free end and the pole second free end. Attached to the pole first free end is a hook for supporting a conventional IV container. Attached to the pole second free end is a clamp which serves to couple the IV support pole to a spinal board. The clamp can be configured to engage a passage lying within the periphery of the spine board, such as a hand passage and/or head end passage such as those commonly found in conventional boards, or can be configured to engage a mounting socket, when such is provided in the board to facilitate attaching the IV support pole thereto.

When the clamp is designed to pass through an existing passage, such as a hand passage, it is preferred for the clamp to have a post, a first restrainer which is affixable to the post and has a cross section so configured that the first restrainer can be positioned so as to be blocked from passing through the passage, and a second restrainer affixable to the post and having a cross section so configured that the second restrainer can be so positioned as to be blocked from passing through the passage, and means for adjusting the separation between the first restrainer and the second restrainer. A preferred means for adjusting the separation between the first restrainer and the second restrainer is to employ a post with a threaded section and provide a nut which can be advanced along the threaded section and so positioned with respect to the restrainers that it acts to advance the restrainers toward each other as it is advanced. The nut can be a separate element or can be integral with one of the restrainers. Having one of the restrainers pivotally mounted to the post can have benefits when it is desirable to install the clamp by passing the restrainer through the passage while engaged with the post. This can be particularly beneficial when that passage is a symmetric passage.

When it is desired to not restrict access to an existing passage in the board, one or more mounting sockets can be provided in the board, and the clamp configured to lockably engage one of the mounting sockets. It is further preferred for multiple mounting sockets to be provided so as to allow variation in the position on the board at which the IV support pole is mounted.

Means for forcibly engaging together the pole segments are provided. When the pole segments are formed as hollow, tubular elements, a preferred means for forcibly engaging together the pole segments is an elastic cord which is threaded through the pole segments and has a cord first end, which is fixably attached with respect to the hook, and a cord second end, which is fixably attached with respect to the clamp. The length of the elastic cord is selected such that the elastic cord is in a stretched condition when the pole segments are assembled to form the rigid extended pole.

One simple structure for the IV support pole of the present invention employs a hook which has a hook extension configured to slidably engage the extended pole first free end, while the clamp for attaching the IV support pole to a spinal board is fitted with a clamp extension which is configured to slidably engage the extended pole second free end. In this case, the elastic cord can be fixably attached to the hook extension and to the clamp extension to assure that they remain engaged with the rigid extended pole.

The IV support pole preferably has a wrap connected to the one of the pole segments to which the hook is attached, the wrap serving to encircle and stabilize an IV container supported by the hook. Means for adjusting the length of the wrap are preferably provided to allow the wrap to be adjusted to tightly encircle an IV container suspended from the hook so as to exert a slight pressure on the container to compensate for the reduced hydrostatic pressure resulting from the use of a relatively short pole to support the IV container. The adjustable wrap can be formed of an elastic material, which can be sized to apply pressure to the IV container when a non-rigid IV container is employed. Preferably, the wrap can also be sized so as to closely encircle the pole segments when the engaging ends of the pole segments are disengaged and the pole segments are positioned side-by-side for more compact storage. In this position, the IV support pole can be conveniently stored in a storage pouch that attaches to the board by pouch straps.

BRIEF DESCRIPTION OF THE FIGURES

FIG. 5 better illustrates the concave upper surface, as well as a concave lower surface central region, spaced-apart spars, and the mounting sockets.

FIG. 7 also more clearly shows a beveled edge of the pad that reduces shear forces on the pad as a patient is loaded onto the pad. FIG. 7 also illustrates a preferred structure for the board, which is formed with a rigid plastic shell that is filled with a foam core.

FIG. 8 is an isometric view of a board which is part of a patient immobilization and transportation system that forms another embodiment of the present invention, the board being viewed from above in FIG. 8. The board has an upper section with a perimeter having protruding regions that aid users in locating hand passages. The board also has mounting sockets located near either end, and a head end passage to facilitate hanging the board for storage and/or for mounting a head immobilizer. The board has a ridge to aid in positioning a pad (the pad is shown in FIG. 10), where the ridge denotes the location of only a portion of the pad, which facilitates flushing and decontamination of the pad and the board.

FIG. 9 is an isometric view of the board shown in FIG. 8, seen from below to better illustrate a pair of spaced apart spars that bound a lower surface central region that is concave.

FIG. 10 is an isometric view of the patient immobilization and transportation system that incorporates the board shown in FIGS. 8 and 9, as well as the pad. FIG. 10 also shows a storage pouch which can be attached to the board by pouch straps to provide convenient storage for an elongated object such as a collapsed IV support pole that can be attached to one of the mounting sockets.

FIG. 11 is a detail view corresponding to the region 11 shown in FIG. 10, illustrating an optional clip pin that can be provided in a strap passage of the board to facilitate attachment of a restraint strap thereto.

FIG. 12 is a partially cut away isometric view of a board similar to the board shown in FIGS. 8–10, but which incorporates stiffening members to increase the longitudinal rigidity of the board. The stiffening members are preferably placed in the spars to avoid increasing the overall thickness of the board and to maintain the stiffening members widely spaced apart. The cut lines in FIG. 12 also show the concave curve of the lower surface central region.

FIG. 13 is an isometric view of a collapsible IV support pole which can be mounted to the mounting socket of a board such as those shown in FIGS. 4–12. The IV support pole is formed from a series of pole segments, a hook, and a clamp, that are connected together by an elastic cord (shown in FIG. 14). The hook can support an IV container, and a wrap secures the IV container to one of the pole segments. The clamp is designed to lockably engage one of the mounting sockets on a board.

FIG. 14 is a partially exploded isometric view of the IV support pole shown in FIG. 13. The wrap is omitted to more clearly show the structure of the remaining elements. The clamp has a central threaded post, on which a nut is threaded, and a retaining pin that protrudes from the threaded post.

FIG. 15 is a top view of the wrap, illustrating sections of hook-and-loop fastener material which allow the wrap to be tightly cinched around an IV container. FIG. 15 also shows the wrap, which is formed from an elastic fabric, engaged with a section of one of the pole segments.

FIG. 16 illustrates the clamp positioned to be slidably engaged with the mounting socket, with the retaining pin oriented to align with opposed pass-through keyways that intersect a cylindrical passage. In this position, the threaded post and retaining pin can be inserted into the mounting socket.

FIG. 17 illustrates the clamp and the mounting socket shown in FIG. 16 after the retaining pin has been passed through the pass-through keyways and the clamp has been turned to align the retaining pin with a pair of opposed positioning keyways. The nut is then turned to lockably engage the mounting socket between the retaining pin and the nut, securing the clamp to the mounting socket.

FIG. 18 is a top view of the mounting socket, while FIG. 19 is an isometric view.

FIG. 24 is an exploded isometric view that illustrates another clamp which can be used to attach an IV support pole to a hand passage (shown in FIGS. 25–27) of a board. This clamp has a bearing flange and a post with a threaded section. The post is slidably engaged by a resilient washer and by a plate with a resilient pad attached thereto. A wing nut threadably engages the post and retains the resilient washer, the plate, and the resilient pad thereon, as shown in FIGS. 25–27.

FIGS. 25 and 26 illustrate the clamp shown in FIG. 24 when the plate and the resilient pad are turned such that they can be passed through the hand passage to the position shown in FIG. 26.

FIG. 27 illustrates the clamp shown in FIGS. 24 through 26 when the plate and the resilient pad have been turned such that they cannot pass through the hand passage. The wingnut is then tightened on the threaded section of the post to forcibly clamp the periphery of the hand passage between the resilient washer, which in turn is forcibly engaged by the bearing flange, and the resilient pad, which in turn is forcibly engaged by the plate.

DETAILED DESCRIPTION OF THE PREFERRED EMBODIMENTS

Figure 1:
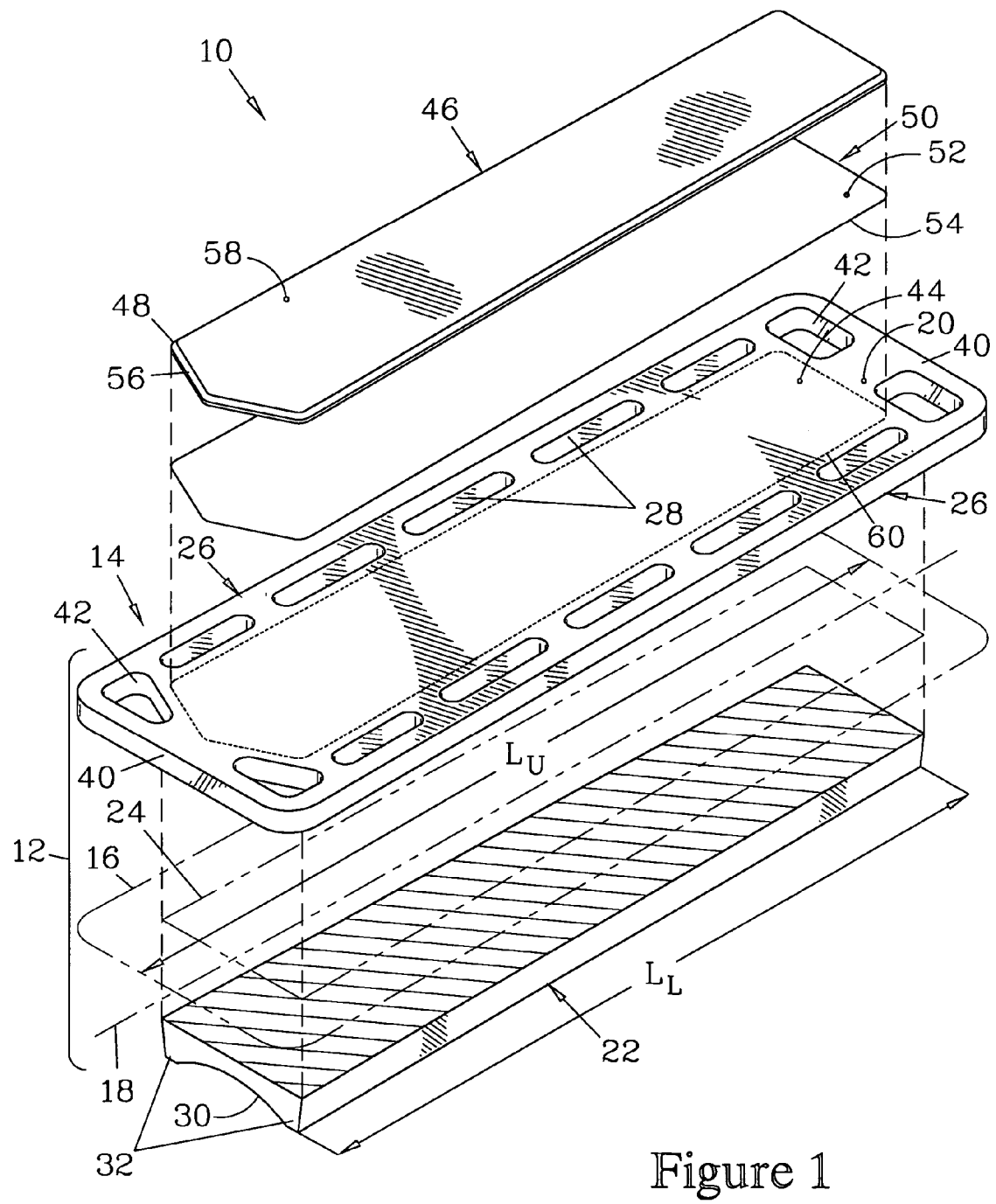
FIG. 1 is an exploded isometric view of a patient immobilization and transportation system that forms one embodiment of the present invention. The system includes a board for supporting the patient and a pad which can be removably attached thereto by an adhesive sheet. The board has an upper section and a lower section, the upper section having a larger footprint to create longitudinal flanges in which hand passages are provided to allow transporting personnel to readily grip the board. The upper section has a planar upper surface to which the pad is attached, while the lower section has a lower surface central region which is concave and is bounded by two spars.
Figure 2:
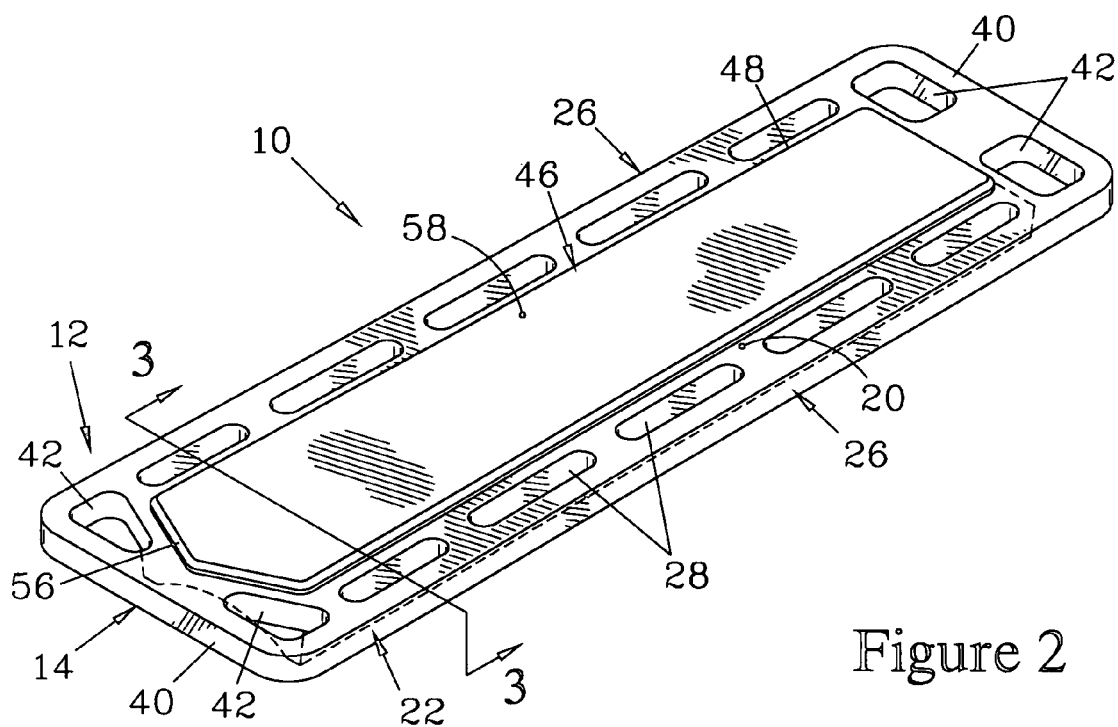
FIG. 2 is an assembled isometric view of the board and the pad illustrated in FIG. 1.

FIG. 1 is an exploded isometric view of a patient transportation and immobilization system 10 of the present invention, while FIG. 2 is an unexploded view of the system 10. The system 10 has a board 12 for support of a patient (not shown). The board has an upper section 14 which has an upper section footprint 16 which is substantially symmetrically disposed about a longitudinal axis 18 and is proportioned to provide full support of a typical patient. Preferably, the upper section is about 18½ inches (470 mm) wide. The upper section 14 is bounded by an upper surface 20 which, in this embodiment, is planar.

Figure 3:
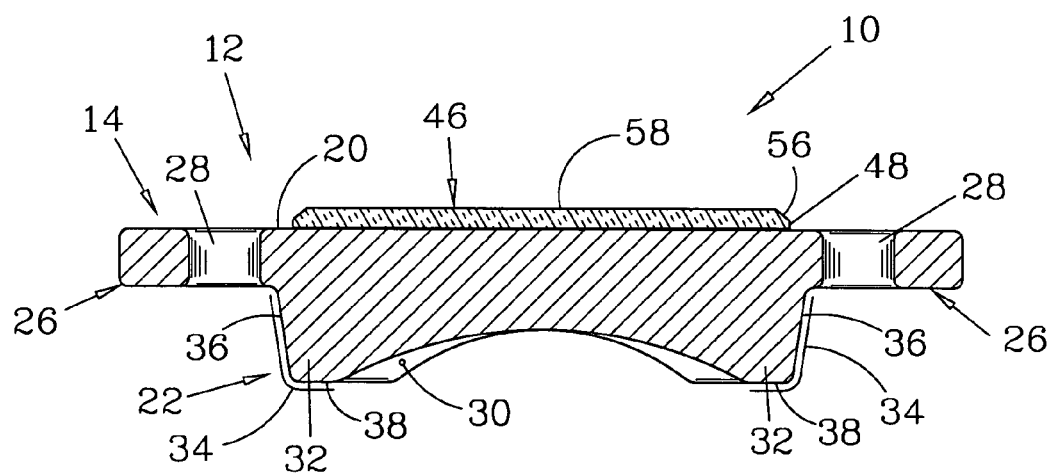
FIG. 3 is a view of the section 3—3 of FIG. 2, better illustrating the planar upper surface and the continuous concave curve of the lower surface central region which enhances the longitudinal rigidity of the board while avoiding creation of x-ray shadows if a patient is examined with x-rays while on the board.

The board 12 has a lower section 22 which has a lower section footprint 24 that is smaller than the upper section footprint 16 and is again substantially symmetrically disposed about the longitudinal axis 18 so as to provide longitudinal flanges 26 on the upper section 14, as best illustrated in FIG. 3 which is a view of the section 3—3 of FIG. 2. These longitudinal flanges 26 extend beyond the lower section 22 and are provided with a series of hand passages 28 which are spaced apart along the longitudinal flanges 26 and provide handgrips to allow transporting personnel to readily grip the board 12.

The lower section 22 is further defined by a lower surface central region 30 (shown in FIG. 3) which is concave when the board is viewed from below. The lower section 22 is also further defined by a pair of spaced apart spars 32 that in turn are each defined by a substantially L-shaped surface 34 that has a first leg 36, which joins one of the longitudinal flanges 26, and a second leg 38, which mates with and continues the lower surface central region 30. Preferably, the first leg 36 is skewed from the vertical to reduce the likelihood of creating x-ray shadows and to provide some degree of draft when the board 12 is fabricated by molding. To further reduce the likelihood of creating x-ray shadows, it is preferred for the joints between the first leg 36 and the longitudinal flange 26, between the first leg 36 and the second leg 38, and between the second leg 38 and the lower surface central region 30 to form continuous smooth curves such that adjacent surfaces meet in such a manner that the slope of the surface continuously changes as it passes across the junction.

The two section board 12 provides multiple benefits to the suitability of the board 12 for the transportation of a patient. The spars 32 assure that the longitudinal flanges 26 are raised above the surface on which the board 12 rests, and thus allow the transporting personnel to readily and securely grasp the board 12 before transporting the patient. The spars 32 also serve to stiffen the board 12, which is further enhanced by joining the spars 32 with the concave lower surface central region 30 that extends between the spars 32. Furthermore, this geometry can be maintained while leaving a relatively open cross section, thus making the board 12 well suited for fabrication by foam filling a rotationally molded shell.

The board 12 of present embodiment also has the lower section 22 configured with a lower section length $L_L$ that is less than an upper section length $L_U$ of the upper section 14, as shown in FIG. 1. This relationship provides end flanges 40 of the upper section 14 that extend beyond the lower section 22 so that corner passages 42 can be provided that are readily accessible from the ends of the board 12, allowing transporting personnel to grip the board 12 for lifting while positioned beyond the end flanges 40. The hand passages 28 and the corner passages 42 surround a cental region 44 (shown in FIG. 1) of the upper surface 20 where the upper surface 20 is continuous.

The spinal immobilization/transportation system 10 has a pad 46 which is configured such that it substantially covers the central region 44 of the upper surface 20 of the board 12, while having a periphery 48 configured such that it will not cover the passages (28 and 42) and interfere with the ability of transporting personnel to readily grip the board 12.

The pad 46 is to be firmly attached to the board 12 so it can withstand shear forces as a patient is slid onto the board 12. However, it is important to enable the pad 46 to be stripped from the board 12 in the event that the pad 46 is damaged in service or becomes contaminated by body fluids. Forming the pad 46 from a fluid-impermeable material helps to reduce the problem of contamination of the pad 46; however, even with this precaution, it is important to be able to remove and replace the pad 46. It is preferred for the pad 46 to be attached to the upper surface 20 with a sheet 50 (shown in FIG. 1) of double-sided adhesive which has a differential tack in the adhesive of the two sides. The upper side 52 of the sheet 50 is provided with the stronger adhesive, and this side is applied to the pad 46. The lower side 54 is provided with the weaker adhesive and is applied to the upper surface 20 to attach the pad 46 thereto. While it is advantageous to have the sheet 50 strippable from the upper surface 20 to allow the pad 46 to be stripped from the board 12, precautions must be taken so as to avoid premature release of the pad 46 to avoid inadvertent stripping while the system 10 is in service. Furthermore, when the pad 46 is stripped, it is preferred that the pad 46 be released with the sheet 50 attached thereto, and thus it is preferred for the stronger adhesive to be associated with the upper side 52 of the sheet 50. It has been found that the adhesion of the lower side 54 to the upper surface 20 of the board 12 can be enhanced by flame treating the upper surface 20 shortly before application of the adhesive sheet 50 thereto. Preferably, the flame treating is done less than about two hours before application of the sheet 50, which has been previously attached to the pad 46.

To reduce the shear forces when the patient is loaded onto the board 12, which might result in stripping of the pad 46 in service, it is preferred that the periphery 48 of the pad 46 be beveled, as best illustrated in FIG. 3. The bevel creates a ramped surface 56 which reduces the cross section of the pad 46 at a front side 58 of the pad 46. This ramped surface 56 reduces the shear force on the pad 46 which results when the patient is slid onto the pad 46, and thereby reduces the likelihood of inadvertent stripping of the pad 46.

Since it is preferred to apply the pad 46 and the sheet 50 to the upper surface 20 after the upper surface 20 has been flame treated to enhance adhesion, it is preferred to provide indicia such as a line 60 (shown in FIG. 1) to form a pad indexing mark that facilitates visual alignment of the pad 46 with the upper surface 20 as the pad 46 is attached thereto. This line 60 can be printed on the upper surface 20 with a heat resistant ink or, alternately, can be a band of plastic having a different color molded into the surface. The latter structure can be achieved by the use of graphic material that is applied to the mold surface and subsequently becomes incorporated into the plastic during the molding process, commercially available from Mold In Graphic Systems of Clarkdale, Ariz.

The system 10 as illustrated requires complementary accessories to secure a patient to the board for transportation and for the immobilization of the patient. These accessories include a series of restraint straps which form a harness for immobilizing a patient on the board, and possibly a head immobilizer and/or additional immobilizing structures that attach to the board; such accessories are currently commercially available and do not form part of the present invention.

Figure 4:
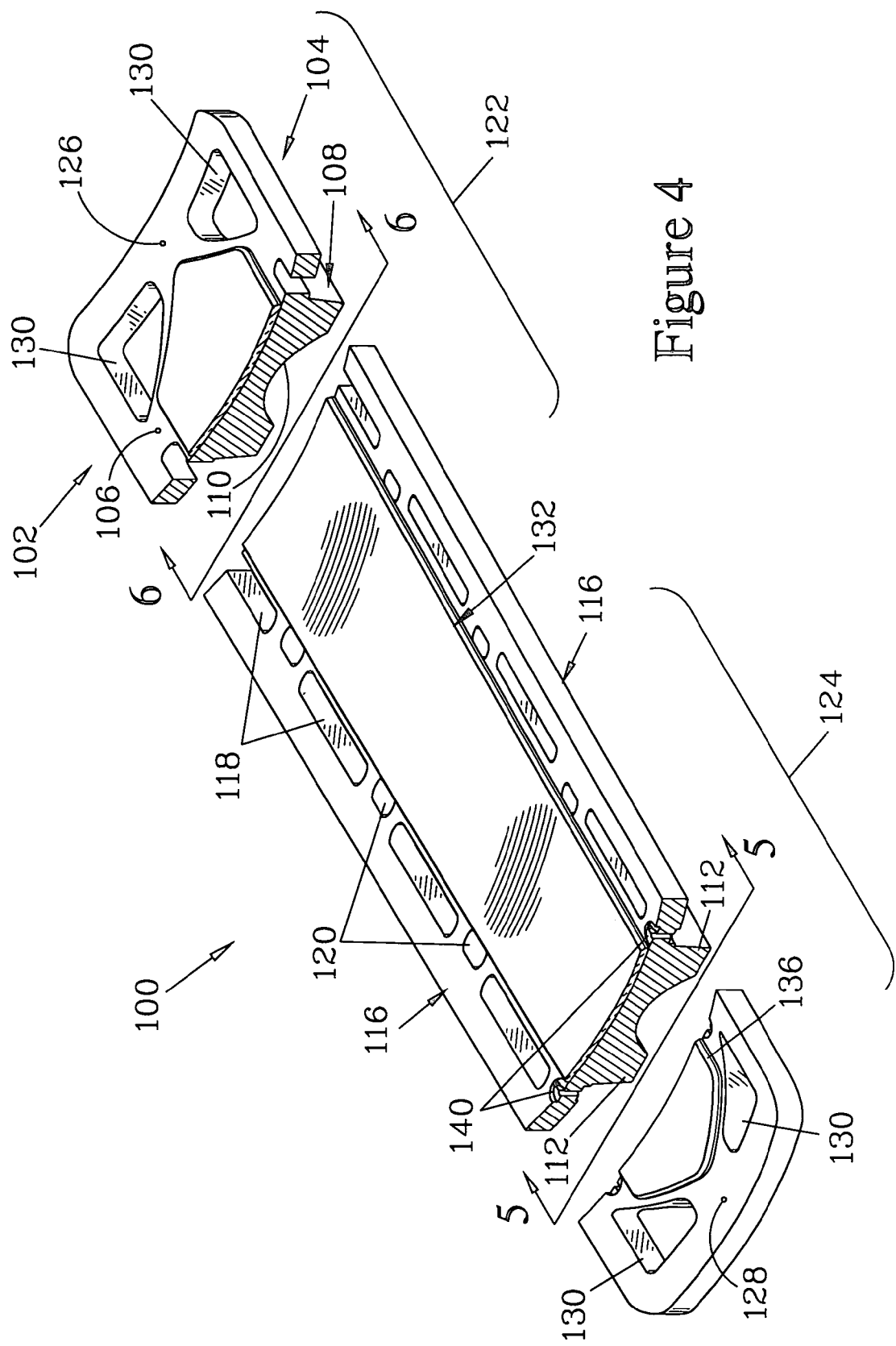
FIG. 4 is a sectioned isometric view of a patient immobilization and transportation system that forms another embodiment of the present invention. Again, the system has a board and a pad removably attached thereto to reduce patient discomfort. In this embodiment, the board has an upper surface that is slightly concave, which serves to better stabilize the patient and further enhance the longitudinal rigidity of the board. The board of this embodiment also has strap passages, to facilitate attachment of restraint straps, and mounting sockets to allow attaching an IV support pole to the board.
Figure 5:
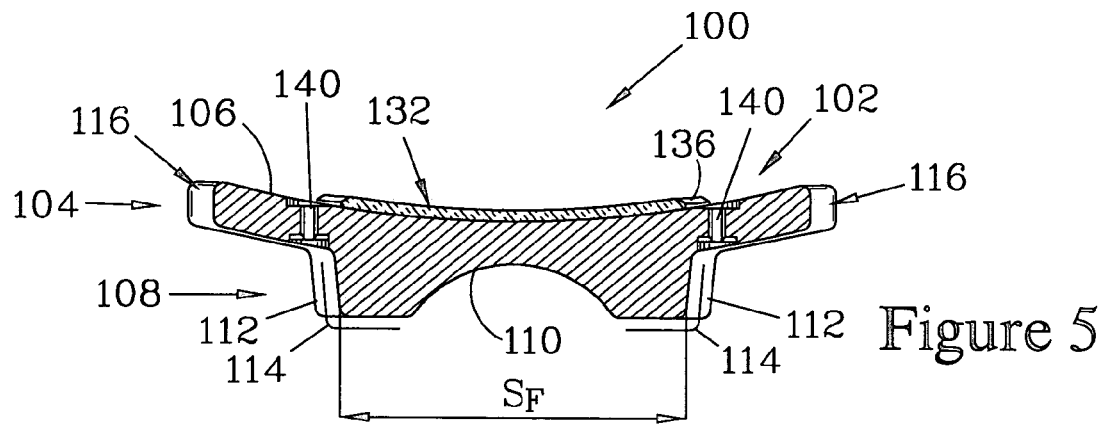
FIG. 5 is a view of the section 5—5 of FIG. 4 through a foot and leg region of the board.
Figure 6:
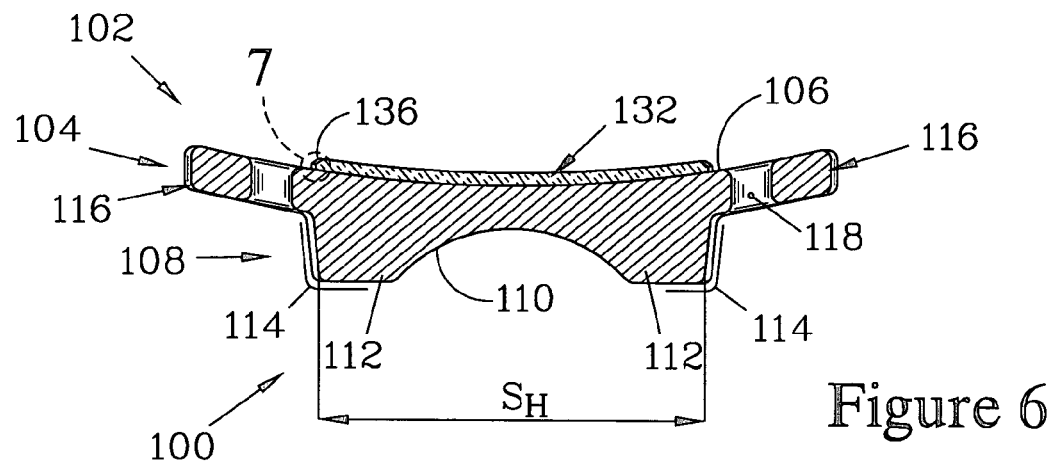
FIG. 6 is a view of the section 6—6 of FIG. 4 through a head and torso region of the board. A comparison to FIG. 5 illustrates the divergence of the spars, which become increasingly spaced apart as they extend through the foot and leg region of the board to the head and torso region. The increased spacing in the head and torso region provides a larger area in the head and torso region that is free from x-ray shadowing, especially in the event that stiffening members are housed in the spars.

FIGS. 4 through 7 form a series of views of a transportation and immobilization system 100. FIG. 4 is an isometric view of the transportation and immobilization system 100 as viewed from above and sectioned into three parts, while FIGS. 5 and 6 are views of the sections. The system 100 has many of the attributes of the embodiment illustrated in FIG. 1 through 3, and has a board 102 having an upper section 104 with an upper surface 106 (best shown in FIGS. 5 and 6) which supports a patient. In this embodiment, the upper surface 106 is slightly concave when viewed from above. The board 102 also has a lower section 108 which, in part, is terminated by a lower surface central region 110 that is concave when viewed from below. The lower section 108 is further bounded by a pair of spars 112 which are defined by substantially L-shaped surfaces 114 and which smoothly join to the lower surface central region 110 and to the upper section 104 so as to provide longitudinal flanges 116.

Referring again to FIG. 4, the longitudinal flanges 116 in turn each have a series of spaced apart hand passages 118 therethrough, which provide a series of spaced apart handgrips to assist transporting personnel in grasping the board 102. Interposed between the hand passages 118 are strap passages 120, which allow for attachment of conventional restraint straps (not shown) to secure a patient to the board 102 and to immobilize the patient to avoid additional injury due to movement. The board 102 has a head and torso region 122 and a leg and foot region 124, with the head and torso region 122 being broader than the leg and foot region 124 to better accommodate the shape of the body of the patient to be supported on the board 102. The upper section 104 is also provided with a head-end flange 126, which terminates the head and torso region 122, and a foot-end flange 128, which terminates the leg and foot region 124. The upper section 104 of the board 102 has corner passages 130 which pass through the head flange 126 and the foot flange 128. These corner passages 130 provide grips that allow transporting personnel to readily carry the board 102 from the ends.

The pair of spars 112 provide multiple benefits to the resulting board 102. They assure that the flanges (116, 126 and 128) are fully accessible for gripping when the board 102 is on the ground and has been loaded. The spars 112 also assist in stiffening the board 102, and the use of the spars 112 in combination with the concave upper surface 106 and the concave lower surface central region 110 can provide adequate rigidity for the resulting board 102 for many applications without the use of additional stiffening members.

In this embodiment, the spars 112 diverge, having a foot region separation $S_F$ (shown in FIG. 5) near the foot-end flange 128 of the board 102, which is less than a head region separation $S_H$ (shown in FIG. 6) near the head-end flange 126 of the board 102. This divergence of the spars 112 as they progress towards the head end of the board 102 provides a larger portion of the cross section of the board 102 in the head and torso region 122 that is free from surfaces with edges that would tend to make x-rays taken through the board more difficult to interpret. It should be appreciated that having the upper section 104 formed with the head and torso region 122 wider than the leg and foot region 124 permits divergence of the spars 112 in the head and torso region 122 without compromising the width of the longitudinal flanges 116.

In this embodiment, a pad 132 is provided which is attached to the upper surface 106 of the board 102. The pad 132 is again attached with a double-sided adhesive sheet 134, shown in FIG. 7. Again, the pad 132 has a beveled periphery 136 which reduces the shear force on the edge as the patient is loaded onto the board 102. In this embodiment, the shear force is further reduced by the curvature of the concave upper surface 106.

Again, indicia are employed to form a pad indexing mark to assist in indexing the pad 132 as it is adhered to the upper surface 106 of the board 102. In this embodiment, the pad indexing mark is formed by a low profile ridge 138 (shown in FIG. 7) which is raised on the upper surface 106 onto which the pad 132 is to be attached. This ridge 138 preferably has a height of not greater than about 0.01 inches so as to maintain the upper surface 106 substantially smooth in the event that the pad 132 is not available when the board 102 is needed for service. This low profile also allows the pad 132 to readily adhere to the upper surface 106 even if the pad 132 is misaligned and crosses the ridge 138. In this embodiment, the ridge 138 does not completely encircle the pad 132, but rather is discontinuous in the leg and foot region 124. Raised indicia are easily incorporated into the mold and will not be subject to thermal derogation, as would printed indicia, and yet because it does not enclose the pad 132, it should allow irrigation and flushing of the pad 132 and the upper surface 106 for cleaning.

In this embodiment, the upper section 104 of the board 102 is provided with two mounting sockets 140 (shown in FIGS. 4 and 5) that are configured for accepting a detachable IV support pole, as discussed in greater detail below with reference to FIGS. 16–19.

Figure 7:
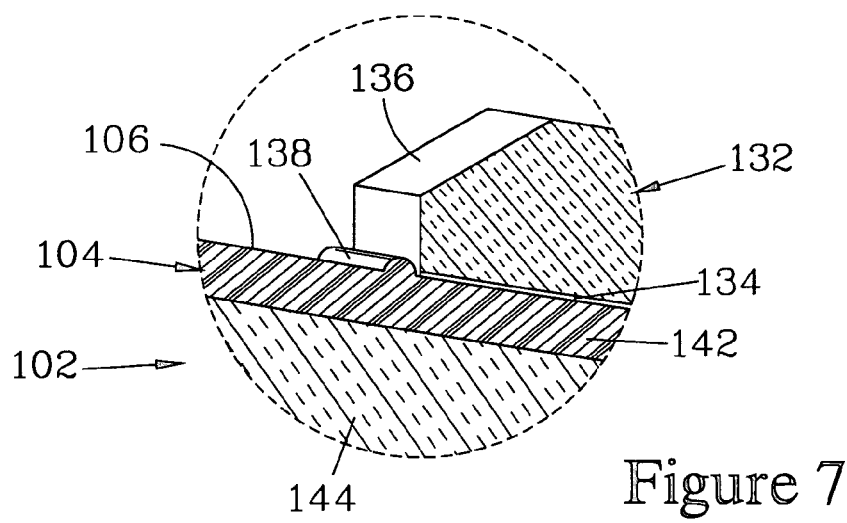
FIG. 7 is a detail view of the region 7 of FIG. 6, illustrating a ridge that serves as a pad indexing mark to facilitate proper placement of the pad on the upper surface of the board.

FIG. 7 illustrates a preferred structure for the board 102, which is shown as having a relatively rigid plastic shell 142 which is filled with a foam core 144. The shell 142 provides a rigid and durable outer surface for the board 102, and the foam core 144 increases the rigidity of the shell 142 while adding only modest additional weight. The shell 142 is preferably formed of a medium density or high density plastic, such as high density polyethylene, and is preferably formed by rotational molding. The foam core 144 is preferably formed from an expanded rigid foam; the two-component expanding foams taught in U.S. Pat. Nos. 5,032,623; 5,194,175; and 5,274,007, incorporated herein by reference, have been found effective. Forming the shell 142 with a wall thickness of at least about 0.08 inches (2 mm) thick with the spars 112 at least about 1½ inches high and 1 inch wide (38 mm×25 mm) should provide the board 102 with sufficient rigidity for most applications when filled with the foam core 144, without requiring the use of additional stiffening members. Furthermore, if stiffening members are to be included, they can be readily housed in the spars 112 prior to adding the foam core 144.

FIGS. 8 and 9 are isometric views of a board 200 that forms part of another embodiment of the present invention, a transportation and immobilization system 202, which is shown in FIG. 10. FIGS. 8 and 10 are views from above the board 200, and FIG. 10 primarily differs from the view of FIG. 8 in that a pad 204 has been attached to the board 200. FIG. 9 is another isometric view of the board 200, where the board 200 is viewed from below. This embodiment has substantially the same elements as the embodiment shown in FIGS. 4 through 7, the board 200 having an upper section 206 and a lower section 208. The board 200 differs principally in the more sculpted lines of the upper section 206 and the lower section 208. The board 200 has longitudinal flanges 210 which are not only more rounded, but which have protruding regions 212 allowing for wider hand passages 214 and serving to accentuate the hand passages 214 to allow them to be more readily located by transporting personnel. The board 200 is also provided with a head end passage 216 through a region of the board 200 where the head of the patient rests; the head end passage 216 can be used to hang the board 200 when stored, and also has utility for other applications such as securing one of straps used to secure a conventional head immobilizer (not shown).

The board 200 is also provided with head-end corner passages 218 and foot-end corner passages 220 which are positioned such that the board 200 can be readily carried from the ends. The head-end corner passages 218 are larger and bifurcated into head-end corner hand passages 222 and head-end corner supplemental passages 224. The present embodiment is also provided with strap passages 226. The strap passages 226 and the head-end corner supplemental passages 224 are provided for attaching conventional restraint straps (not shown) to the board 200 for securing and restraining the patient on the board 200. These passages (224, 226) can each be provided with a clip pin 228, as illustrated in FIG. 11, to facilitate rapid connection of a restraint strap to the board 200 in the manner known in the art.

FIG. 8 shows a full view of an upper surface 230 of the upper section 206. The upper surface 230 is concave when the board 200 is viewed from above. This concave upper surface 230 aids in stabilizing the patient and better conforms to the body shape of the patient for reduced discomfort. The concave upper surface 230 also serves to stiffen the board 200. The upper surface 230 is provided with an indexing ridge 232 to aid in the application of the pad 204 to the board 200. Since the pad 204 is designed to attach on contact and to substantially cover the area of the upper surface 230 between the hand passages 214 and the strap passages 226, and since the upper surface 230 is concave, it is important to be able to accurately locate the pad 204 on the upper surface 230 when it is brought in contact with the board 200. Furthermore, the indexing ridge 232 as shown is configured so as not to form a closed region, since such might interfere with drainage if the pad 204 and upper surface 230 are flushed to wash away body fluids, making decontamination of the board 200 easier than for boards where the pads are maintained in depressions.

FIG. 9 illustrates the positions of a pair of spars 234 that form part of the lower section 208. In this embodiment, the spars 234 diverge as they approach the region of the board 200 designed to support the head and torso of the patient. This view also illustrates a concave lower surface central region 236 of the board 200.

FIG. 12 illustrates a board 200' which is similar to the board 200, but which is fitted with stiffening members 238. The stiffening members can be carbon fiber tubes, such as are discussed in U.S. Pat. No. 5,950,627, which teaches the use of divergent carbon fiber tubes for strengthening a board. Other suitable stiffening members include fibreglass tubes, hickory rods, or similar rigid cylindrical members such as are known in the art. The stiffening members 238 are housed in the spars 234'. The boards (200, 200') each have a relatively open cross section and are well suited to fabrication by rotationally molding a shell 240 and subsequently filling the shell 240 with a foam core 242. In fact, when the shell 240 has an average wall thickness t that is at least about 0.08 inches (2 mm), and the spars 234 are at least about 1½ inches high and 1 inch wide (38 mm×25 mm), the board 200' has sufficient rigidity for most applications even when the stiffening members 238 are not included.

The boards 200 and 200'are each designed to be fitted with an IV support pole (not shown) and, for these embodiments, both a pair of head-end mounting sockets 244 and a pair of foot-end mounting sockets 246 are provided. These mounting sockets (244 and 246) allow an IV container to be supported near any of the four limbs of the patient for administrating fluids intravenously. FIG. 10 also illustrates a storage pouch 248 which can contain such an IV support pole when collapsed. The storage pouch 248 illustrated attaches to the board 200 by pouch straps 250 that pass through the hand passages 214 to secure the storage pouch 248 on the underside of the longitudinal flange 210.

FIGS. 13 and 14 are isometric views of an IV support pole 300 of the present invention which is configured to be employed with one of the boards (100, 200, 200') shown in FIGS. 4 through 12 to provide a transportation and immobilization system. The IV support pole 300 is collapsible for storage, and is shown in FIG. 14 in its collapsed configuration (in a partially exploded view), suitable for compact storage in a pouch such as the storage pouch 248 discussed above. The IV support pole 300 is formed from a series of tubular pole segments 302 having engaging ends 304 (shown in FIG. 14) configured such that, when aligned, the pole segments 302 can be engaged together to form a rigid extended pole 300' (shown in FIG. 13) terminating in a pole first free end 306 and a pole second free end 308. In this embodiment, the engaging ends 304 are male and female ends that are configured such that they can slidably engage. Other engagement schemes could be employed, such as bayonet connections or threaded connections. However, it is preferred for the engaging ends 304 to be slidably engageable for ease of fabrication and ease of assembly/disassembly of the IV support pole 300. When the pole segments 302 are formed from lengths of tube stock, the male engaging ends 304' can be readily formed by swaging one end of the pole segment 302 so as to reduce the cross section of the male engaging end 304' sufficiently to slidably engage a non-reduced segment of the pole segment 302 that forms the female engaging end 304".

The pole first free end 306 has a hook 310 attached thereto, which is designed to support an IV container 312 (illustrated in FIG. 13) for supplying an IV solution to a patient. The pole second free end 308 is attached to a clamp 314 (best shown in FIG. 14) which, in this embodiment, is configured to slidably engage a mounting socket 316 (shown in FIGS. 16–19) which is similar to the mounting sockets 140 shown in FIGS. 4 and 5 and the mounting sockets (244 and 246) shown in FIGS. 8–10, and which is discussed in greater detail below.

The hook 310 has a hook extension 318 which, in this embodiment, has a cylindrical cavity 320 configured to slidably engage and rest on the pole first free end 306. As shown in FIG. 14, the clamp 314 has a clamp extension 322 which, in this embodiment, is formed as a stub having a cylindrical section 324 that is configured to slidably engage a central passage 326 of the IV support pole 300 and engage the pole second free end 308.

An elastic cord 328 is provided for maintaining the pole segments 302 compressibly engaged together when the pole segments 302 are aligned and slidably engaged. The elastic cord 328 is passed through the central passage 326 and has a cord first end 330, which is attached to the hook extension 318, and a cord second end 332, which is attached to the clamp extension 322. The elastic cord 328 is selected to have a length such that, when the pole segments 302 are slidably engaged with each other and with both the hook extension 318 and the clamp extension 322, the elastic cord 328 is in tension when attached between the hook extension 318 and the coupling extension 320. The elastic cord 328 provides means for forcibly engaging together the pole segments 302. Since the hook 310 and the clamp 314 are slidably engaged with pole segments 302 in this embodiment, the elastic cord 328 also serves to forcibly engage the hook 310 and the clamp 314 with the pole segments 302.

Since the IV support pole 300 is intended to be used in transit to deliver fluids to the patient, it is preferred that the rigid extended pole 300' be relatively short so as not to substantially raise the IV container 312 above the board, in order to maximize the freedom in moving the patient and to stabilize the IV container 312 while the patient is in transit. In the present embodiment, the hook 310 is provided with a hook extending arm 334 to help reduce the likelihood of the IV container 312 becoming disconnected from the hook 310 in service. To further assure the stability of the IV container 312, it is preferred to provide a wrap 336 (shown in FIGS. 13 and 15), which encircles the IV container 312 and the IV support pole 300 to stabilize the container 312 with respect to the IV support pole 300 and the board during transport of a patient. The wrap 336 is connected to the pole segment 302' which has the hook 310 attached thereto. In this embodiment, the wrap 336 is formed from an elastic fabric 338. The elastic fabric 338 is sewn to form an elastic mounting loop 340 sized to tightly encircle the pole segment 302', as shown in FIG. 15, and the elastic fabric 338 preferably has piping 342 to prevent fraying.

Means for adjusting the length of the wrap 336 are preferably provided; in this embodiment, the means for adjusting the length of the wrap 336 include a section of loop material 344 and a series of hook material strips 346 sewn to the elastic fabric 338. The hook material strips 346 are positioned along the elastic fabric 338 and can be selectively engaged by the loop material 344 to provide a hook-and-loop closure in the manner well known in the art. Thus, the loop material 344 can be attached to selected hook material strips 346 to size the wrap 336 such that the container 312 can be snugly engaged by the wrap 336. Preferably, the wrap 336 is sized such that, when encircling the IV container 312, the elastic fabric 338 is in tension so as to exert a positive pressure on the IV container 312 to promote flow of fluids from the IV container 312 to compensate for the limited hydrostatic head. It should be appreciated that the relative locations of the loop material 344 and the hook material strips 346 could be reversed, and other closure structures known in the art, such as snaps, could be employed.

The wrap 336 is also designed to provide a second function, and that is to bundle the pole segments 302 when they are disengaged (in the position shown in FIG. 14), so that they will remain in a side-by-side relationship so that they can be readily stored in a compact form. When so wrapped, the IV support pole 300 can be readily stored in a pouch such as the storage pouch 248 discussed above and shown in FIG. 10.

Figure 16:
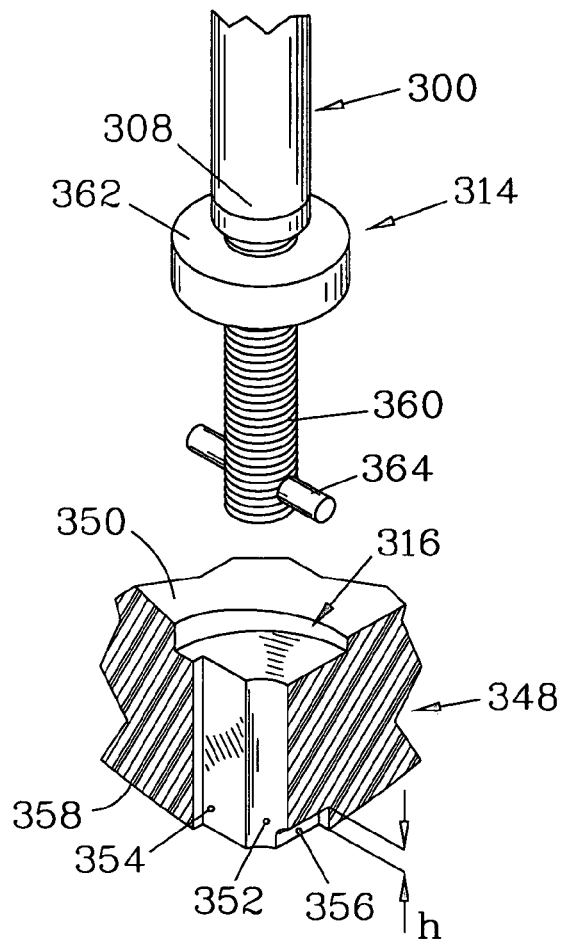
FIGS. 16 and 17 are partially sectioned isometric views illustrating how the clamp shown in FIGS. 13 and 14 lockably engages the mounting socket.
Figure 17:
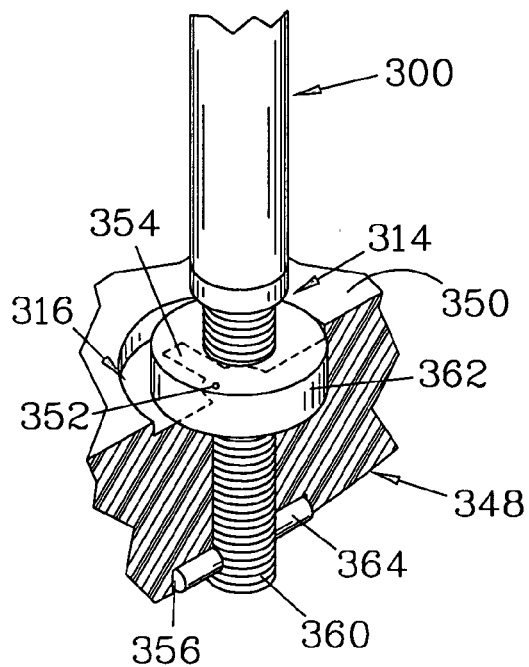
Figure 18:
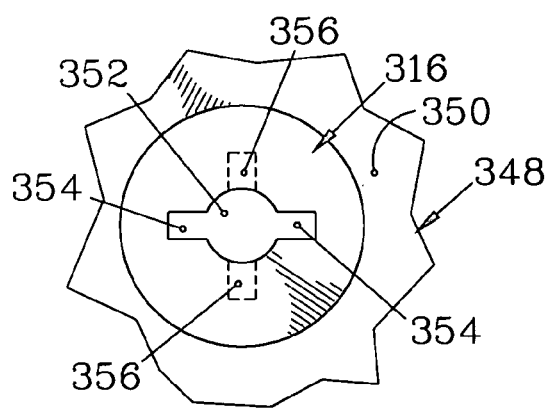
FIGS. 18 and 19 are views of the mounting socket shown in FIGS. 16 and 17, better illustrating the cylindrical passage and the keyways.
Figure 19:
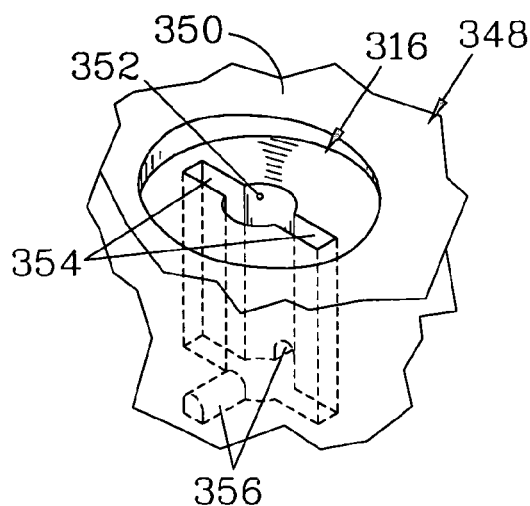
Figure 20:
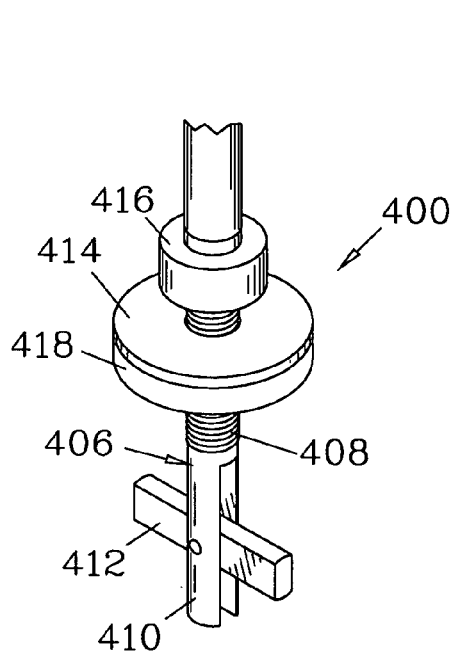
FIG. 20 illustrates a clamp which does not require a mounting socket to be provided in the board. This clamp is particularly well suited for attaching to a symmetric hole such as a head end passage, which is frequently found in spineboards, but can also attach to a hand passage, as illustrated in FIGS. 21 and 22. The clamp has a post with a threaded section and a slotted free end, in which a retaining bar is pivotably mounted. A bearing flange slidably engages the post, and a nut engages the threaded section. A resilient washer is attached to the bearing flange.

FIGS. 16 through 19 illustrate further details of the mounting socket 316, which is similar in details to one of the mounting sockets (244 and 246) illustrated in FIGS. 8–10, and is formed in a portion of a longitudinal flange 348 which is similar to one of the longitudinal flanges 210 shown in FIGS. 8–10. FIGS. 16 and 17 are sectioned isometric views of the clamp 314 and the mounting socket 316, FIG. 18 is a top view of the mounting socket 316 as it exits an upper surface 350 of the longitudinal flange 348, and FIG. 19 is an unsectioned isometric view of the mounting socket 316. The mounting socket 316 has a cylindrical passage 352 intersected by a pair of diametrically opposed pass-through keyways 354 which extend through the longitudinal flange 348. On the bottom of the longitudinal flange 348, there is a pair of diametrically opposed positioning keyways 356 that are rotationally offset from the pass-through keyways 354. These positioning keyways 356 terminate at a height h from a bottom surface 358 of the longitudinal flange 348.

The clamp 314 is designed for attaching to the mounting socket 316, which is inset into the longitudinal flange 348. The clamp 314 slidably engages and lockably engages the mounting socket 316, affixing the IV support pole 300 to the longitudinal flange 348, as shown in FIG. 17. The clamp 314 has a threaded post 360 configured such that it will readily slide into the cylindrical passage 352 of the mounting socket 316. The threaded post 360 in turn is threadably engaged by a nut 362 which serves as a first restrainer that is sized to prevent passage of the threaded post 360 through the cylindrical passage 352 in one direction.

The threaded post 360 is fitted with a retaining pin 364 which passes through and extends from the threaded post 360. The retaining pin 364 is sized to pass through the pass-through keyways 354. Once passed through the pass-through keyways 354, the threaded post 360 can be turned to reposition the retaining pin 364 such that it can be engaged with the positioning keyways 356 (as shown in FIG. 17) and serves as a second restrainer, which in this position prevents passage of the threaded post through the cylindrical passage 352 in the other direction. The nut 362 is then tightened to forcibly engage the longitudinal flange 348 between itself and the retaining pin 364, thereby securing the IV support pole 300. In this embodiment, the threadable engagement of the nut 362 with the threaded post 360 serves as means for adjusting the separation between the first restrainer and the second restrainer. It is also noteworthy that, in this embodiment, the nut 362 provides a first restrainer which cannot pass through the cylindrical passage 352 regardless of its position.

While the IV support pole 300 illustrated has the clamp 314 that is suitable for attaching to a particular mounting socket configuration, the IV support pole of the present invention has utility for a broad class of boards. In fact, since spineboards generally have passages that provide hand grips and/or allow hanging the board, by the use of an appropriate clamp it is possible to mount an IV support pole internal to the periphery of the board to provide an IV support pole that is at least partially protected from impacts as the board is transported.

Figure 21:
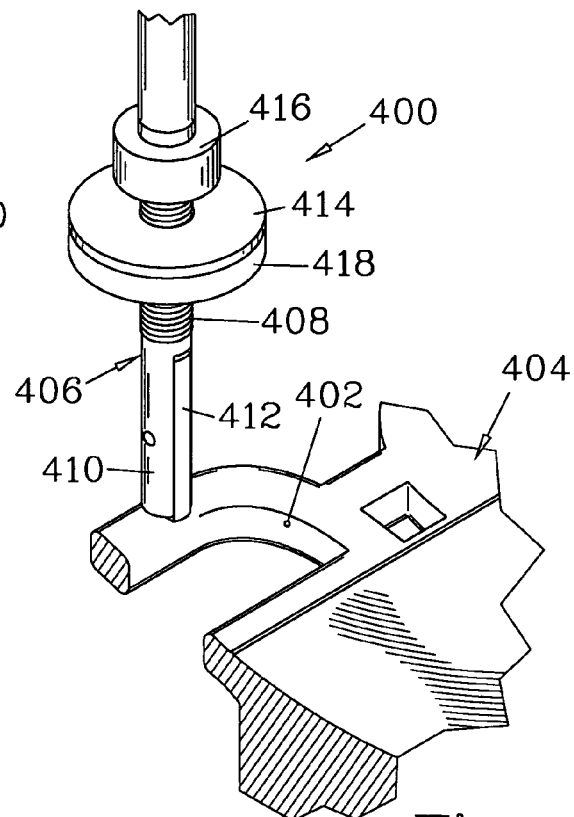
FIG. 21 illustrates the clamp shown in FIG. 20 when the retaining bar is pivoted so as to partly reside within the slotted free end of the post, allowing it to be readily passed through a passage such as the hand passage illustrated. The bearing flange is sufficiently large that it cannot pass through the hand passage.
Figure 22:
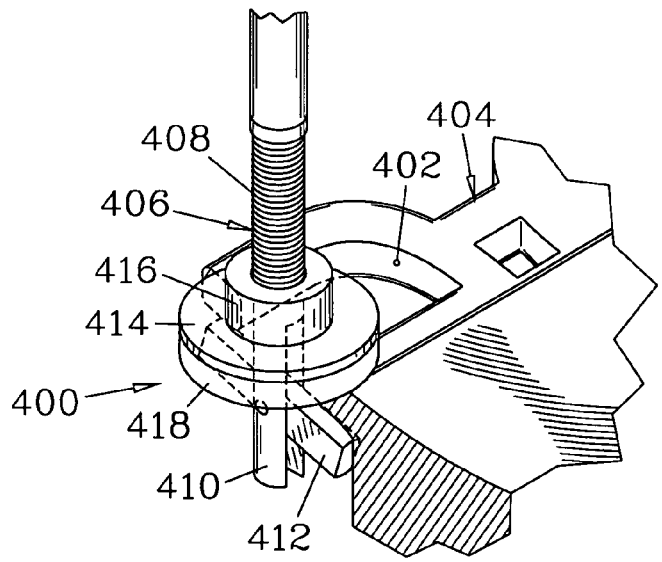
FIG. 22 illustrates the clamp shown in FIGS. 20 and 21 when the retaining bar has been passed through the hand passage and then pivoted so as to engage the periphery of the hand passage. The nut is then turned to force the bearing flange toward the retaining bar, which results in the periphery of the hand passage being clamped between the retaining bar and the resilient washer on the bearing flange.

FIGS. 20–23 illustrate one example of a clamp 400 that is designed to pass through a passage 402 in a board 404 (only partially shown), which is shown as a hand passage in FIGS. 21 and 22. The clamp 400 has a post 406 having a threaded section 408 and terminating in a slotted free end 410 into which is pivotally mounted a retaining bar 412 which serves as a first restrainer that is pivotably mounted. A bearing flange 414 slidably engages the post 406 and serves as a second restrainer. A nut 416 is threadably engaged with the threaded section 408 of the post 406 and serves to adjust the separation between the retaining bar 412 and the bearing flange 414. Preferably, the bearing flange 414 is provided with a resilient washer 418 to allow the clamp 400 to better conform to the surface of the board 404 that is engaged by the clamp 400.

Figure 23:
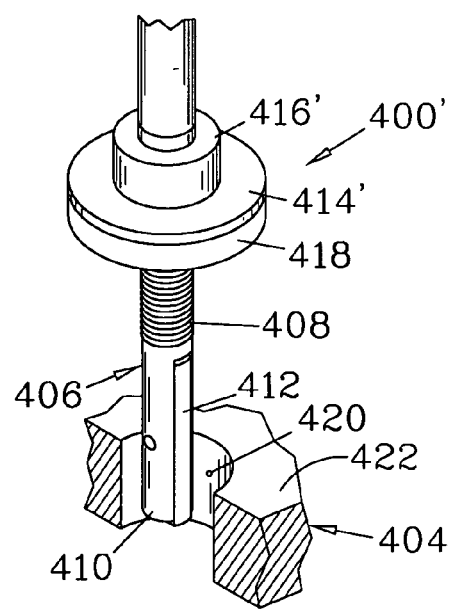
FIG. 23 illustrates the clamp shown in FIGS. 20 through 22 partially inserted into a symmetrical head end passage of the board, the head end passage being provided to allow hanging the board for storage and/or to facilitate attaching a head immobilizer to the board.

The configuration of the clamp 400 has particular utility when the clamp is to be mounted in a passage which is symmetric. FIG. 23 illustrates a clamp 400' partially inserted into a symmetrical head end passage 420 which is provided to allow hanging the board 404 for storage. The clamp 400' differs in that the bearing flange 414' is rotatably attached to the nut 416' to prevent inadvertent loss of the bearing flange 414'. The rotatable attachment of the bearing flange 414' to the nut 416' allows the nut 416' to be readily turned when the resilient washer 418 on the bearing flange 414' engages an upper surface 422 of the board 404.

FIGS. 24–27 illustrate another clamp 500, which has particular utility when used to fasten an IV support pole 502 to a board 504 through a hand passage 506. Again, the clamp 500 has a post 508 having a threaded section 510, and a bearing flange 512 is affixed to the post 508, serving as a first restrainer. In turn, a resilient washer 514 is attached to the bearing flange 512. A wing nut 516 is theadably engaged with the threaded section 510. A plate 518 having a resilient pad 520 attached thereto is provided, which serves as a second restrainer. The plate 518 slidably engages the threaded section 510 of the post 508, and is positioned between the wing nut 516 and the resilient washer 514. The plate 518 has a major axis and a minor axis configured such that the plate 518 can be passed through the hand passage 506 when the minor axis is substantially normal to a longitudinal axis of the hand passage 506, the orientation illustrated in FIGS. 25 and 26. However, when the plate 518 is positioned with its minor axis substantially parallel to the longitudinal axis of the hand passage 506, as shown in FIG. 27, it cannot pass through the hand passage 506, and the wing nut 516 can be tightened on the threaded section 510 to adjust the separation between the plate 518 and the bearing flange 512 so as to clamp the board 504 between the plate 518 and the bearing flange 512.

While the novel features of the present invention have been described in terms of particular embodiments and preferred applications, it should be appreciated by one skilled in the art that substitution of materials and modification of details obviously can be made without departing from the spirit of the invention.

What I claim is:

1. A spinal immobilization board comprising:
   an upper section which has an upper section footprint which is symmetrically disposed about a longitudinal axis and proportioned to support the patient, said upper section being bounded by a substantially planar upper surface;
   a lower section having a lower section footprint that is smaller than said upper section footprint and also symmetrically disposed about said longitudinal axis, thereby forming longitudinal flanges bounding said upper section, said lower section being bounded by a central lower surface which is concave when viewed from below said board and is longitudinally terminated by a pair of spaced apart spars that join said central lower surface to said longitudinal flanges; and
   a series of hand passages passing through said longitudinal flanges, forming handgrips for said board.

2. The spinal immobilization board of claim 1 wherein said upper surface of said upper section is slightly concave when viewed from above.

3. The spinal immobilization board of claim 2 wherein said upper section has a upper section length $L_U$ and further wherein said lower section has a lower section length $L_L$ such that: $L_U > L_L$, thereby providing end extensions of said upper section, said board further comprising:
   corner hand passages in said end extensions.

4. The spinal immobilization board of claim 3 wherein said board has a head end and a foot end and further wherein said spars diverge such that the separation between said spars increases as the distance from said foot end increases.

5. The spinal immobilization board of claim 4 wherein said spars are defined by substantially L-shaped surfaces, each having a first leg which joins one of said longitudinal flanges and a second leg which joins to said central lower surface, said joints providing a smooth transition between said first leg and said longitudinal flange and between said second leg and said central lower surface, said first leg and said second leg being joined together so as to provide a smooth transition therebetween.

6. The spinal immobilization board of claim 5 wherein said first leg of each of said substantially L-shaped surfaces is skewed with respect to said one of said longitudinal flanges to which said first leg joins.

7. The spinal immobilization board of claim 6 wherein said board further comprises:
   a shell of a rigid plastic formed by rotational molding which forms an exterior surface of said board, said shell having a wall thickness of at least about 0.08 inches; and
   a foam core filling said shell.

8. The spinal immobilization board of claim 7 wherein said shell is formed from high density polyethylene and said foam core is formed by a blown rigid foam.

9. The spinal immobilization board of claim 8 further comprising:
   a stiffening member housed in each of said spars.

10. The spinal immobilization board of claim 3 wherein each of said longitudinal flanges further comprises:
    protruding regions adjacent to said hand passages, said protruding regions and said hand passages being configured to provide hand grips.

11. The spinal immobilization board of claim 10 wherein each of said longitudinal flanges further comprises:
    restraint strap passages interposed between said hand passages.

12. A spinal immobilization system for supporting a patient, the spinal immobilization system comprising:
a board having,
an upper section which has an upper section footprint which is symmetrically disposed about a longitudinal axis and proportioned to support the patient, said upper section being bounded by a substantially planar upper surface,
a lower section having a lower section footprint that is smaller than said upper section footprint and also symmetrically disposed about said longitudinal axis, thereby forming longitudinal flanges bounding said upper section, said lower section being bounded by a central lower surface which is concave when viewed from below said board and is longitudinally terminated by a pair of spaced apart spars that join said central lower surface to said longitudinal flanges, and
a series of hand passages passing through said longitudinal flanges, forming handgrips for said board;
a fluid-impermeable pad configured such that its periphery can be positioned so as to reside on said upper surface of said board, said pad being removably affixable thereto; and
indicia on said upper surface of said board positioned to serve as a pad indexing mark for aligning said fluid-impermeable pad so as to be symmetrically located within said handgrips.

13. The spinal immobilization system of claim 12 wherein said pad indexing mark is formed by one or more ridges raised on said upper surface and configured so as to avoid forming a closed area, and
further wherein said fluid impermeable pad has an adhesive back side for removably attaching to said upper surface of said board and a front side on which a patient to be immobilized rests, said fluid impermeable pad having a beveled edge which slopes toward said front side.

14. The spinal immobilization system of claim 13 further comprising:
a sheet having a first adhesive side for adhering to said pad; and
a second adhesive side serving as said adhesive back side of said pad when said sheet is adhered to said pad, said second adhesive side having a weaker adhesive than said first adhesive side.

15. The spinal immobilization system of claim 12 wherein said pad indexing mark is formed by one or more grooves in said upper surface, and
further wherein said fluid impermeable pad has an adhesive back side for removably attaching to said upper surface of said board and a front side on which a patient to be immobilized rests, said fluid impermeable pad having a beveled edge which slopes toward said front side.

16. The spinal immobilization system of claim 12 further comprising:
an IV support pole for supporting a conventional IV container with respect to said board, said IV support pole having,
a series of pole segments which are joinable to form a rigid extended pole having a pole first free end and a pole second free end, each of said pole segments having adjoining portions with mating ends which can be engaged together;
a hook attaching to said pole first free end and configured to support a conventional IV container;
a clamp for attaching said IV support pole to said upper section of said board, said clamp attaching to said extended pole second free end; and
means for forcibly engaging together said pole segments.

17. The spinal immobilization system of claim 16 further comprising:
at least one mounting socket provided in said upper section of said board, and
further wherein said clamp lockably engages said mounting socket.

18. The spinal immobilization system of claim 16 further comprising:
a storage pouch for storing said IV support pole when said pole segments are disengaged from each other, said storage pouch having pouch straps for attaching to said hand passages of said board.

* * * * *